United States Patent [19]

Ohtani et al.

[11] Patent Number: 4,476,222
[45] Date of Patent: Oct. 9, 1984

[54] TEST PIECE FOR QUANTITATIVE ANALYSIS OF SUBSTANCES IN BODY FLUIDS

[75] Inventors: Mikio Ohtani, Machida; Hiroshi Wada, Chigasaki; Yuzo Kosaka, Tokyo, all of Japan

[73] Assignee: Eiken Kagaku Kabushiki Kaisha, Tokyo, Japan

[21] Appl. No.: 423,745

[22] Filed: Sep. 27, 1982

[30] Foreign Application Priority Data

Aug. 2, 1982 [JP] Japan .................................. 57-134953

[51] Int. Cl.³ ......................... G01N 33/52; C12Q 1/28
[52] U.S. Cl. ........................................ 435/14; 422/56; 435/25; 435/26; 435/28; 435/805
[58] Field of Search ...................... 422/56, 57; 435/14, 435/26, 805, 25, 28

[56] References Cited

U.S. PATENT DOCUMENTS

| 3,092,465 | 6/1963 | Adams et al. | 23/253 |
| 3,298,789 | 1/1967 | Mast | 23/253 |
| 3,616,251 | 10/1971 | Lecco et al. | 422/56 X |
| 3,926,736 | 12/1975 | Bucolo | 435/26 |
| 3,971,702 | 7/1976 | Maekawa et al. | 435/14 |
| 4,268,411 | 5/1981 | Iwata et al. | 422/42 X |
| 4,283,491 | 8/1981 | Dappen | 422/56 X |
| 4,312,834 | 1/1982 | Vogel et al. | 422/56 |
| 4,318,985 | 3/1982 | Bauer et al. | 422/56 X |
| 4,372,746 | 2/1983 | Habenstein | 422/56 X |

Primary Examiner—Arnold Turk
Attorney, Agent, or Firm—Quaintance & Murphy

[57] ABSTRACT

A testing piece for quantitative analysis of a substance in a body fluid, particularly in blood, said testing piece comprising an absorbent carrier containing in it reagents for measuring the substance and coated with a mixture of polymethylmethacrylate and polyvinyl formal. This testing piece enables the efficient and swift quantitative analysis of the substance in body fluid, especially in blood, in a short time without preliminary separating the serum from the blood.

20 Claims, 1 Drawing Figure

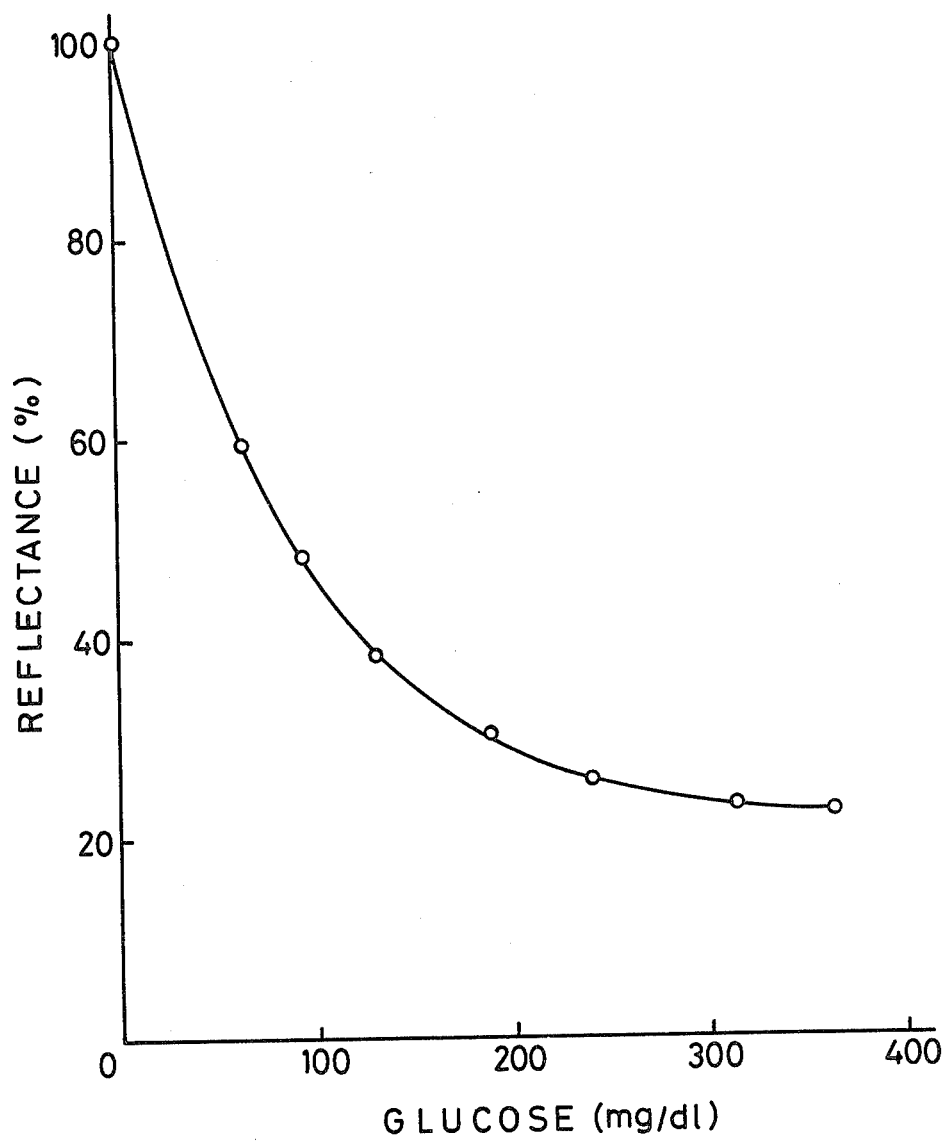

TEST PIECE FOR QUANTITATIVE ANALYSIS OF SUBSTANCES IN BODY FLUIDS

BACKGROUND OF THE INVENTION

1. Field of the Invention

The present invention relates to a test piece for measuring a substance in a body fluid, particularly in blood.

2. Prior Art

Heretofore, for the purpose of measuring a specific substance or substances in body fluids, especially in blood, it has been necessary to separate serum from blood and add a freshly prepared measuring reagent to this serum. Such operations were complicated and time-consuming. At the same time, if the blood or serum has been left for a long time before the start of analysis or if it takes time to prepare serum samples, the substances to be measured are often destroyed or changed and accurate quantitative analysis cannot be made. Further, many of the reagents used for measurements have a problem that they lack the stability after preparation, which forces a great waste of the reagents.

For solving these various problems, there have come into wide use the so-called test pieces in which reagents for detecting the intended substance are contained in an absorbent carrier such as filter paper. Among such test pieces, there is one in which the absorbent carrier impregnated with a measuring reagent is coated with an appropriate coating material so that when the coated carrier is brought into contact with blood, the substance to be measured separates from blood, i.e. the substance penetrates into the carrier leaving blood cells on the coated surface to permit the reaction with the measuring reagent. In such a test piece, the results of the reaction can be judged immediately after the reaction, by removing the blood cells on the carrier surface, through washing with water. Therefore, it enables the measurement in an extremely short time by using a small amount of blood without separating serum.

For example, in the case of diabetics, it is regarded therapeutically important to measure glucose in blood of the patient and determine the dosage of medicine to be administered based on the results of the measurement. This purpose may be achieved by using the aforesaid test piece.

As described above, it is considered that test pieces which permit the use of the whole blood as a specimen are desirable for rapid analysis. However, the technical difficulty in putting such test pieces into practical use lies in that no suitable coating material has heretofore been known which enables the swift and efficient separation of the substance to be measured from blood.

For example, there is known such technique that an absorbent carrier containing a measuring reagent is coated with a cellulose derivative such as ethylcellulose (U.S. Pat. Nos. 3,092,465 and 3,298,789). However, according to this method, strict selection is required with respect to the content of the substituents in the cellulose derivative and its viscosity in order to adjust the permeability of the substance to be measured (glucose), which is accompanied by a great difficulty from an aspect of preparing the coating materials. Further, the coated test pieces are usually cut into sizes suitable for actual use. But when the cellulose derivative is employed as the coating material, there is a problem that blood penetrates into the carrier through the cutting plane on measurement, and accordingly the results of the measurement tend to be deviated from the correct values.

On the other hand, it is also known a technique to employ a substance other than the cellulose derivative for the separation of a substance to be measured from the blood cells (Japanese Patent Publication No. 15669/1970). According to this method, the surface of a carrier containing a reagent for detecting the intended substance is coated with a hydrophobic substance such as fats and oils, wax, silicone etc. The disadvantage of this method is that since the hydrophobic properties of these substances are so strong that the permeability of the substance to be measured is excessively retarded and hence it takes unduly long time for measurement.

As the result of the intensive study for the purpose of solving the above-described problems, the present inventors have accomplished the present invention.

SUMMARY OF THE INVENTION

An object of the present invention is to provide a test piece for quantitative analysis of substances in body fluid, especially in blood, which enables the measurement in a short time without preliminary separation of serum from the blood.

Another object of the present invention is to provide a test piece for quantitative analysis of substances in body fluid, especially in blood, which enables the substances to separate from the body fluid efficiently and swiftly and penetrate into the test piece.

Still another object of the present invention is to provide a test piece for quantitative analysis of substances in body fluid, especially in blood, wherein the permeability of the substances into the test piece can be adjusted as required, thereby enabling the control of the reaction speed of the substance and a measuring reagent contained in the test piece.

According to the present invention, an absorbent carrier containing a measuring reagent therein is coated with a mixture of polymethylmethacrylate and polyvinyl formal; the ratio of which may be selected from the range between 1:9 and 9:1.

These and other objects and features of the present invention will be more apparent to those skilled in the art to which the invention pertains upon consideration of the accompanying drawing and following specification wherein is disclosed an exemplary embodiments of the present invention with the understanding that such variations and modifications may be made therein as fall within the scope of the appended claims without departing from the spirit of the invention.

BRIEF DESCRIPTION OF THE DRAWING

A FIGURE is a calibration curve obtained by the use of a test piece A in Example 1 wherein the ordinate denotes reflectance at 700 nm and the abscissa denotes the concentration of glucose in blood.

DETAILED DESCRIPTION OF THE INVENTION

Now, the present invention will be explained more in detail, in conjunction with the drawing, based upon specific examples which are never interpreted as limiting the scope of the invention.

The present invention has been accomplished on the basis of the acknowledgement that when the carrier containing in it a reagent to measure the intended substance is coated with the mixture of polymethylmethacrylate and polyvinyl formal, the test piece thus obtained enables the efficient separation of the intended substance from the blood into the carrier in a short time.

According to the present invention, since relatively hydrophilic polymethylmethacrylate and hydrophobic polyvinyl formal are used in combination as the coating material, the coating material which gives desired permeability of the substance to be measured may be readily obtained by changing the mixing ratio of both components, and hence the reaction rate may be easily adjusted consequently.

Where polymethylmethacrylate is used alone as the coating material, the blood cells readily penetrates into the carrier through the cut plane of the test piece as in the case of the cellulose derivative, whereas in the case where polyvinyl formal is used alone as the coating material, an effective coating is not formed on the test piece and therefore the blood cells can not be adequately removed. Considering the above facts, the excellent effects obtained by the mixing of both components is quite beyond expectations and the coating material in the present invention has superior features to any other known coating materials.

The substances in blood which can be measured by the test piece according to the present invention may include glucose, galactose, pyruvic acid, amino acids, lactic acid, alcohol, urea etc., and the reagents to be used for measurement are determined individually depending on the intended substance to be measured. For example, a test piece for measuring glucose in blood contains glucose oxidase, a substance having peroxidase activity and an oxidizable indicator as basic ingredients. Similarly, a test piece for measuring galactose in blood contains galactose oxidase, a substance having peroxidase activity and an oxidizable indicator. On the other hand, in the case where the alcohol level in blood is to be measured, a test piece is impregnated with a reagent comprising alcohol dehydrogenase, nicotine adenine dinucleotide, diaphorase and a tetrazolium salt. In most cases, the method for measuring a specific substance is not limited to only one, and a plurality of methods are known. Any method may be applied as long as the reagent can be contained in the carrier in a stable state. Further, it is known to add a substance to buffer the reagent composition to a constant pH, a substance to stabilize it, a substance to adjust its reaction rate etc., and it is well appreciated to those skilled in the art that the present invention may be easily modified based on such conventional knowledge.

The polymethylmethacrylate to be used in the present invention is a polymer of methyl methacrylate, which is a resin with excellent transparency and stability and is applied as organic glass. On the other hand, the polyvinyl formal is a condensate of polyvinyl alcohol and formaldehyde, and it is put into practical use as electrically insulating materials. Desirable molecular weights of both substances are selected in view of the removal of the blood cells from whole blood. However, its selection does not need to be so strict since the desired blood cell separation characteristics may be readily obtained by changing the mixing ratio of both substances. While the mixing ratio of the polymethylmethacrylate to the polyvinyl formal in terms of weight may be freely varied within the range of from 1:9 to 9:1, it is most preferred to use both in approximately equal amounts.

The test piece of the present invention may be obtained by impregnating an absorbent carrier with a reagent for measurement and coating it with the coating material. Examples of the absorbent carrier are filter paper, cotton, wood chips, synthetic fiber paper, glass fiber, porous plastics etc., among which filter paper is the most preferred material.

In producing the test piece according to the present invention, the impregnation step and the coating step may be practiced either in one stage or in two or more stages. The coating material is applied, preferably in the final stage, as dissolved in an organic solvent such as acetone, methylene chloride, chloroform etc. In this case, it is also possible to mix a part of the measuring reagent into the solution of the coating material. After the impregnation, the carrier is dried under appropriate conditions. The obtained carrier is adhered to an appropriate supporting sheet using an adhesive tape if necessary, and it is cut into appropriate sizes for practical use.

The test piece thus cut is substantially free from impregnation with blood via the cut plane. The reason therefor is considered as follows:

In case polymethylmethacrylate is employed alone, the coating on the cut plane and its vicinity is likely to be broken in cutting. Consequently, blood cell may penetrate into the carrier via the cut plane. On the other hand, in case the mixture of polymethylmethacrylate and polyvinyl formal is employed, both constitute an elastic coating while they are adequately tangled with each other. Thereby, the degree that the coating on the cut plane is broken is lowered and the blood is substantially prevented from penetrating into the carrier via the cut plane.

The supporting sheet may be of any material although it is desired to show less water absorption. Wood, paper, cloth, metal, glass and preferably plastic material such as polystyrene, polyethylene, polyvinyl chloride etc. may be used. This sheet is not an indispensable feature of the present invention, but it serves to protect the testing piece and at the same time increase its utility.

On measuring the substances in blood, the reaction is effected by dropping a certain amount of blood taken from the earlobe or the finger tip onto a test piece and allowing it to stand for a predetermined time. Then, after washing off the blood with water and wiping the remaining water with clean paper etc., the concentration of the substance may be estimated by comparing the density of the color thus produced with the standard color chart which is prepared separately. Alternatively, it is also possible to measure the reflectance of the produced color at a predetermined wavelength by means of an appropriate measuring instrument and determine the concentration of the substance with reference to the concentration-reflectance curve which is prepared separately.

The following examples are given to more particularly describe the present invention, but it should be noted that the present invention is not limited to these examples.

EXAMPLE 1

Test Pieces for Measuring Glucose in Blood

In order to demonstrate the effectiveness of the coating material used in the present invention, test pieces for measuring glucose in blood were prepared.

Filter paper No. 2316 manufactured by Schleicher and Schüll AG was dipped in the following first solution and dried at 60° C. for 30 minutes.

| First Solution | |
| --- | --- |
| Glucose oxidase (12000 IU/g) | 0.83 g |
| Peroxidase (105 IU/mg) | 0.038 g |
| Polyvinylpyrrolidone (MW 40,000) | 5 g |
| O—Tolidine dihydrochloride | 0.3 g |
| 2,7-Diaminofluorene dihydrochloride | 0.2 g |
| Citric acid | 1.98 g |
| Sodium citrate | 5.22 g |
| EDTA · 2Na | 0.1 g |
| Ethanol | 28 ml |
| Distilled water | (Distilled water added so that total volume may be 100 ml) |

The obtained test paper was divided into four sections, one of which was dipped in the following second solution and dried at 40° C. for 10 minutes.

| Second Solution | |
| --- | --- |
| Polymethylmethacrylate | 0.75 g |
| Polyvinyl formal | 0.75 g |
| Methylene chloride | (Methylene chloride added so that total volume may be 100 ml) |

Thus obtained test paper was adhered to a polystyrene supporting sheet. Then it was cut to prepare a test piece having a test portion of 5 mm×10 mm. This is designated test piece A (Invention). For the remaining three sections impregnated with the first solution, similar procedures were conducted except that the coating materials were changed. That is, instead of the mixture of polymethylmethacrylate and polyvinyl formal in the second solution, 1.5 g of polymethylmethacrylate only, 1.5 g of polyvinyl formal only, and 1.5 g of ethyl cellulose alone were employed to prepare test pieces as, designated B, C and D (Controls), respectively.

Fresh blood was dropped onto the test portion of each test piece, washing was done with water 60 seconds after the dropping, the remaining water was removed by absorbing with clean filter paper. Thereafter, the state of each test portion was observed. The results are set forth in Table 1.

TABLE 1

| Test Piece | Removal of Blood Cells from the Surface | Permeation of Blood Cells through the Cut Plane |
| --- | --- | --- |
| A (Invention) | Completely removed | No |
| B (Control) | Almost removed | Observed |
| C (Control) | Insufficiently removed | No |
| D* (Control) | Almost removed | Observed |

*U.S.P. 3,092,465 and 3,298,789

As shown above, the test piece according to the present invention was most excellent in the removal of blood cell from its surface and sufficiently prevented the permeation of blood cells through the cut plane.

Thereafter, test piece A described in Example 1 was subjected to the reaction with several blood specimens having different concentrations of glucose exactly for 60 seconds, and washed with water and the remaining water was wiped off with clean filter paper. Immediately thereafter, the reflection factors were measured using a color analyzer (Hitachi Color Analyzer Model 607) at a wavelength of 700 nm. A calibration curve shown in the FIGURE was obtained from the reflectance and the corresponding glucose concentrations measured by a glucose analyzer (YSI Glucose Analyzer Model 23-A).

EXAMPLE 2

Test Piece for Measuring Pyruvic Acid in Blood

Filter paper was dipped in the following first solution and immediately lyophilized.

| First Solution | |
| --- | --- |
| Monopotassium phosphate | 3.408 g |
| Disodium phosphate | 0.852 g |
| Pyruvic acid oxidase (15 IU/mg) | 2 g |
| Peroxidase (105 IU/mg) | 0.143 g |
| Gum arabic | 2 g |
| Flavin adenine dinucleotide | 0.25 g |
| Distilled water | (Distilled water added so that total volume may be 100 ml) |

Thereafter, it was dipped in the following second solution and in dried vacuum.

| Second Solution | |
| --- | --- |
| 3,3',5,5'-Tetramethylbenzidine | 0.35 g |
| Polymethylmethacrylate | 0.6 g |
| Polyvinyl formal | 0.6 g |
| Methylene chloride | (Methylene chloride added so that total volume may be 100 ml) |

A test piece adhered to a plastic was obtained following the procedures similar to those in Example 1. When this was subjected to a reaction with blood containing pyruvic acid for 120 seconds and washed with water, a clear blue color was observed. The density of which was proportional to the content of pyruvic acid.

EXAMPLE 3

Test Piece for Measuring Galactose in Blood

The following first solution and second solution were successively applied to a filter paper. Drying was carried out at 50° C. for 30 minutes and for 5 minutes respectively after the applications of the first and second solutions. Thereafter, the procedures similar to those in Example 1 were conducted to obtain a test piece.

| First Solution | |
| --- | --- |
| Galactose oxidase (250 IU/mg) | 0.1 g |
| Peroxidase (105 IU/mg) | 0.095 g |
| Monopotassium phosphate | 2.177 g |
| Disodium phosphate (dodecahydrate) | 1.433 g |
| Gelatin | 0.5 g |
| Distilled water | (Distilled water added so that total amount may be 100 ml) |
| Second Solution | |
| 2,7-Diaminofluorene | 0.5 g |
| Polymethylmethacrylate | 0.4 g |
| Polyvinyl formal | 0.6 g |
| Chloroform | (Chloroform added so that total amount may be 100 ml) |

This test piece exhibited a blue color with blood containing galactose, and its density corresponds to the galactose content.

Having now particularly described and ascertained the nature of our said invention and in what manner the same is to be performed, we declare that what we claim is:

1. A test piece for quantitative analysis of a substance in body fluid, said test piece comprising: an absorbent carrier, reagents for measuring the substance, said reagents being contained in said absorbent carrier, and a coating on a surface of the absorbent carrier, said coating comprising polymethylmethacrylate and polyvinyl formal.

2. A test piece for quantitative analysis of a substance in body fluid claimed in claim 1, wherein the weight ratio of polymethylmethacrylate to polyvinyl formal in the coating is between 9:1 and 1:9.

3. A test piece for quantitative analysis of a substance in body fluid claimed in claim 2, wherein said weight ratio is around 1:1.

4. A test piece for quantitative analysis of a substance in body fluid claimed in claim 1 wherein the absorbent carrier is a member selected from the group consisting of filter paper, cotton, wood piece, synthetic fiber paper, glass fiber, and porous plastics.

5. A test piece for quantitative analysis of a substance in body fluid claimed in claim 4, wherein the absorbent carrier is filter paper.

6. A test piece for quantitative analysis of a substance in body fluid claimed in claim 1 wherein a surface of said test piece is carried by a plastic sheet.

7. A test piece for quantitative analysis of a substance in body fluid claimed in claim 1 wherein said reagent comprises glucose oxidase, a substance having a peroxidase activity, and an oxidizable indicator.

8. A test piece for quantitative analysis of a substance in body fluid claimed in claim 4, wherein said reagent comprises glucose oxidase, a substance having a peroxidase activity, and an oxidizable indicator.

9. A test piece for quantitative analysis of a substance in body fluid claimed in claim 6, wherein said reagent comprises glucose oxidase, a substance having a peroxidase activity, and an oxidizable indicator.

10. A test piece for quantitative analysis of a substance in body fluid claimed in claim 1 wherein said reagent comprises galactose oxidase, a substance having a peroxidase activity, and an oxidizable indicator.

11. A test piece for quantitative analysis of a substance in body fluid claimed in claim 4, wherein said reagent comprises galactose oxidase, a substance having a peroxidase activity, and an oxidizable indicator.

12. A test piece for quantitative analysis of a substance in body fluid claimed in claim 6, wherein said reagent comprises galactose oxidase, a substance having a peroxidase activity, and an oxidizable indicator.

13. A test piece for quantitative analysis of a substance in body fluid claimed in claim 1 wherein said reagent comprises alcohol dehydrogenase, nicotine ademine dinucleotide diaphorase and a tetrazolium salt.

14. A test piece for quantitative analysis of a substance in body fluid claimed in claim 4, wherein said reagent comprises alcohol dehydrogenase, nicotine ademine dinucleotide, diaphorase, and a tetrazolium salt.

15. A test piece for quantitative analysis of a substance in body fluid claimed in claim 6, wherein said reagent comprises alcohol dehydrogenase, nicotine ademine dinucleotide, diaphorase and a tetrazolium salt.

16. A test piece for quantitative analysis of a substance in body fluid, comprising:

A. an absorbent carrier; and
B. a reagent in said absorbent carrier, said reagent being glucose oxidase, a substance having a peroxidase activity, and an oxidizable indicator; and
C. a coating on a surface of the absorbent carrier, said coating comprising polymethylmethacrylate and polyvinyl formal, wherein the weight ratio of polymethylmethacrylate to polyvinyl formal is between 9:1 and 1:9.

17. A test piece for quantitative analysis of a substance in body fluid, comprising:

A. an absorbent carrier; and
B. a reagent in said absorbent carrier, said reagent being galactose oxidase, a substance having a peroxidase activity, and an oxidizable indicator; and
C. a coating on a surface of the absorbent carrier, said coating comprising polymethylmethacrylate and polyvinyl formal, wherein the weight ratio of polymethylmethacrylate to polyvinyl formal is between 9:1 and 1:9.

18. A test piece for quantitative analysis of a substance in body fluid, comprising:

A. an absorbent carrier; and
B. a reagent in said absorbent carrier, said reagent being alcohol dehydrogenase, nicotine ademine dinucleotide diaphorase and a tetrazolium salt; and
C. a coating on a surface of the absorbent carrier, said coating comprising polymethylmethacrylate and polyvinyl formal, wherein the weight ratio of polymethylmethacrylate to polyvinyl formal is between 9:1 to 1:9.

19. A test piece for quantitative analysis of glucose in body fluid comprising:

A. an absorbent carrier, said absorbent carrier being filter paper; and
B. a reagent in said absorbent carrier, said reagent comprising glucose oxidase, a substance having a peroxidase activity, and an oxidizable indicator; and
C. a coating on a surface of the absorbent carrier, said coating comprising polymethylmethacrylate and polyvinyl formal, the weight ratio of polymethylmethacrylate to polyvinyl formal being 1:1.

20. A test piece for quantitative analysis of a substance in body fluid, said test piece comprising:

A. an absorbent carrier, wherein said absorbent carrier is a member selected from the group consisting of filter paper, cotton, wood piece, synthetic fiber paper, glass fiber, and porous plastics; and
B. a reagent in said absorbent carrier, said reagent comprising:
  1. a substance having a peroxidase activity,
  2. an oxidizable indicator, and
  3. a member selected from the group consisting of glucose oxidase, pyruvic acid oxidase, galactose oxidase, and alcohol dehydrogenase; and
C. a coating on a surface of the absorbent carrier, said coating comprising polymethylmethacrylate and polyvinyl formal, wherein the weight ratio of polymethylmethacrylate to polyvinyl formal is between 9:1 and 1:9.

* * * * *